United States Patent
Madere

(10) Patent No.: US 7,214,666 B1
(45) Date of Patent: May 8, 2007

(54) COMPOSITION OF ORALLY ADMINISTERED NUTRITIONAL SUPPLEMENTS TO REPAIR ARTICULAR CARTILAGE

(76) Inventor: Shawn Paul Madere, 1067 Jackstown Rd., Paris, KY (US) 40361

( * ) Notice: Subject to any disclaimer, the term of this patent is extended or adjusted under 35 U.S.C. 154(b) by 753 days.

(21) Appl. No.: 10/129,245

(22) PCT Filed: Nov. 2, 2000

(86) PCT No.: PCT/US00/30268

§ 371 (c)(1),
(2), (4) Date: Apr. 29, 2002

(87) PCT Pub. No.: WO01/32188

PCT Pub. Date: May 10, 2001

Related U.S. Application Data

(60) Provisional application No. 60/162,948, filed on Nov. 2, 1999.

(51) Int. Cl.
*A61K 31/70* (2006.01)
*A61K 31/10* (2006.01)

(52) U.S. Cl. .................... 514/62; 514/708; 514/825

(58) Field of Classification Search ................. 514/62, 514/708, 825
See application file for complete search history.

(56) References Cited

U.S. PATENT DOCUMENTS

| | | |
|---|---|---|
| 3,683,076 A | 8/1972 | Rovati |
| 3,697,652 A | 10/1972 | Rovati et al. |
| 4,973,605 A | 11/1990 | Herschler |
| 5,162,303 A | 11/1992 | Goodman |
| 5,364,845 A | 11/1994 | Henderson |
| 5,587,363 A | 12/1996 | Henderson |
| 5,840,715 A | 11/1998 | Florio |
| 5,843,923 A | 12/1998 | Schleck et al. |
| 5,902,801 A | 5/1999 | Schleck et al. |
| 5,916,565 A | 6/1999 | Rose et al. |
| 5,922,692 A | 7/1999 | Marino |
| 6,136,795 A | 10/2000 | Florio |
| 6,451,771 B1 * | 9/2002 | Henderson et al. ........... 514/54 |
| 6,797,289 B2 * | 9/2004 | Henderson et al. ......... 424/757 |

FOREIGN PATENT DOCUMENTS

| | | |
|---|---|---|
| EP | 0214642 A2 | 3/1987 |
| WO | WO-98/52556 A1 | 11/1998 |

OTHER PUBLICATIONS

Bucci, Luke R.;"Chondroprotective Agents Glucosamine Salts and Chondroitin Sulfates", Townsend Letters for Doctors, pp. 52-54, Jan. 1994.
Colgan, Michael, "Glucosamine Saves Your Joints", Muscular Development, Fitness Health, vol. 31, No. 8, p. 24, Aug. 1994.
Bucci, Luke R.; "Glucosamine—A New Potent Nutraceutical For Connective Tussues", The Nutritional Supplement Advisor, Jul. 1992.

* cited by examiner

*Primary Examiner*—Raymond J. Henley, III
(74) *Attorney, Agent, or Firm*—Stockwell & Smedley, PSC

(57) ABSTRACT

Provided is a synergistic combination of nutritional supplements classified as Nutraceuticals and further combined with antioxidant vitamins and minerals that, when orally administered to mammals, provides optimal delivery of vital metabolic precursors necessary for the production and repair of articular cartilage. Specifically provided is, a unique combination of chondroitin sulfate sodium, methylsulfonylmethane, glucosamine potassium, glucosamine hydrochloride, glucosamine sulfate sodium, N-acetyl D-Glucosamine, sodium absorbate and chelated manganese proteinate compounded through agitation. The provided compositions and methods of administration are designed to effectively elevate and sustain blood levels of said compounds in turn enhancing the body's natural chondroprotective mechanisms while providing an efficient delivery mechanism which optimizes cellular uptake of glucosamine and chondroitin. This process of forming specified synergistic relationships between vital metabolic precursors increases the body's production of proteoglycans, chondrocytes, hyalauron glycosaminoglycans and collagen, facilitating the repair and regeneration of articular cartilage and symptomatic relief from pain and inflammation associated with articular degeneration.

23 Claims, No Drawings

COMPOSITION OF ORALLY ADMINISTERED NUTRITIONAL SUPPLEMENTS TO REPAIR ARTICULAR CARTILAGE

This application claims the benefit of priority in U.S. Provisional Application Ser. No. 60/162,948, filed Nov. 2, 1999.

FIELD OF INVENTION

The present invention is directed to compositions of nutritional supplements. Specifically, the invention relates to a unique compound that, when ingested by mammals, is capable of repairing and regenerating articular cartilage, resulting in relief from associated symptoms of articular cartilage degeneration.

BACKGROUND OF THE INVENTION

The connective joints of mammals can be categorized as one of the following types:
(1) Fixed or structured joints such as those found in the plates of the skull;
(2) Amphiarthroidal or limited mobility joints such as those of the pelvis or sacroiliac; and
(3) Diarthroidal or Synovial joints. These joints are highly mobile consisting of, hinge, ball and socket, saddle or gliding joints; such as knee, hip, and carpal joints. These highly mobile joints have similar structures and components including, "the joint capsule," this is the outer membrane, which encases the joint and connects one bone to the other. "The Synovium" is the inner lining of the joint capsule which secretes synovial fluid. Molecules of hyaluronic acid are responsible for the viscosity of the synovial fluid and play a crucial role in maintaining healthy cartilage and protecting the joint surface. Articular cartilage is a matrix of proteoglycans, chondrocytes, and collagen, which caps the articulating ends of the bones. Articular cartilage absorbs shock from mechanical forces and provides a viscous surface so that bone ends may glide easily across one another. Ligaments, tendons, muscles, and bursae provide structure and stabilization to the joints as well. All must function properly together to insure ease of movement and longevity for the joint.

Our primary concern is the status of the articular cartilage. When healthy, articular cartilage forms a smooth, slick surface for the bone ends providing pain free movement and resilience. Many variables influence the viability of articular cartilage including, mechanical forces, trauma, disease, aging, and osteoarthritis. In all such cases, the integrity of the articular cartilage may be compromised. As the healthful qualities of articular cartilage diminish, wear is inevitable. Bone surfaces become coarse resulting in painful afflictions of inconvenience, inflammation, and in extreme cases incapacitation.

Articular cartilage is compromised of 65–80% water, collagen, proteoglycans, and chondrocytes. Collagen comprises microscopic fibers found in all tissues such as skin, tendons ligaments, and joint cartilage. This versatile protein provides elasticity and the structural framework of the cartilage matrix. Proteoglycans are molecules of protein and amino sugars, interwoven with collagen fibers to form the articular cartilage. Due to their dense negative ion content, these molecules are able to attract and retain water within the cartilage formation specifically for lubrication.

Proteoglycans provide the unique mechanical properties for resiliency and recovery under compressive forces. Chondrocytes are active cells within the cartilage, which manufacture new collagen and proteoglycan molecules while excreting enzymes, which remove damaged cartilage and proteoglycan molecules. Chondrocytes also produce synovial fluid for nutrient transportation and hyalauran lubrication. Synovial cells work in concert with chondrocytes to produce hyaluronan; also known as hyaluronic acid. This important glycosaminoglycan (GAG) is an integral part of both synovial fluid and articular cartilage. Within the articular cartilage, hylauronan provides viscoelastic properties allowing ease of motion between opposing surfaces and increasing compressive resistance. Within the synovium, hyaluronic acid as synovial fluid provides an effective barrier regulating the introduction of plasma components. Under normal conditions, the body will synthesize sufficient amounts of base components to maintain and regenerate articular cartilage, while limiting the production and release of destructive proteinases and enzymes. Yet, with the onset of degeneration, the demand for these base components becomes taxed and supplementation becomes necessary. Supplementation being the addition of metabolic precursors to the diet, aiding in the biosynthesis of proteoglycans, GAG's, hylauron, and collagen.

Metabolic precursors for the production of articular cartilage include, chondroitin sulfate, a glycosaminoglycan polysaccharide, which is a primary component of articular cartilage comprising an aminosugar and an organic acid or sugar. Specifically chondroitin sulfate is broken down into sulfate disaccharides and N-Acetyl galactosamine. Glucuronic acid is the key substrate comprising one half of the hyaluronan molecule, the other being N-Acetyl D-glucosamine. Chondroitin sulfate, as CS4 and CS6 within the body, are a critical class of glycosaminoglycans which bind water to the articular cartilage matrix and are necessary for the formation of proteoglycans.

Glucosamine, as glucosamine 5-phosohate, is naturally occurring within the body. It is fundamental catalyst for the biosynthesis of glycosaminoglycans, proteoglycans, hyaluronan, and collagen. Glucosamine is the primary amino sugar found in tissues and articular cartilage. Glucosamine is available in exogenous forms, glucosamine sulfate sodium, glucosamine hydrochloride and N-Acetyl D-Glucosamine. These forms are highly bioavailable in mammals. The remaining exogenous form, glucosamine hydroiodide, is not well tolerated or assimilated.

Each compound demonstrates properties unique in origin and activity within the body. Glucosamine sulfate sodium, glucose and an amine bound to sodium sulfate, is made bioavailable by catalyzing the conversion of glucosamine to GAGs. Glucosamine hydrochloride, an amino derivative obtained by chemical hydrolysis of hydrochloric acid on disaccharides, is bioavailable for the production of hyaluronic acid, N-Acetyl D-Glucosamine, a two amino derivative of glucose obtained by chemical hydrolysis of chitin, a polysaccharide and sub-component of hyaluronic acid. Glucosamine sulfate potassium, an aminosugar composition bound to the mineral potassium, facilitates cellular membrane function and sustained release of primary substrates (glucosamine) for collagen and proteoglycan synthesis. Methylsulfonymethane (MSM), the most bio-available sulfur compound found in the body, is an integral part of hemoglobin and body tissue, and is essential for the synthesis of connecting tissues, collagen and the essential amino acids methionine and cysteine. Utilized as an antiinflammatory and blood vessel dilator, exogenous MSM influences cellular membrane potentials relating to cellular transfer of sodium and potassium. Manganese proteinate is a peptide bound mineral which catalyzes GAG and collagen synthesis. Sodium ascorbate is an electrolyte bound ascorbate needed for collagen production and aids in the body's ability to utilize manganese.

The biosynthesis of these metabolic precursors follow specific pathways to produce new articular cartilage while regulating the damaging effects of destructive enzymes. Exogenous glucosamine allows the body to exceed the natural rate-limiting thresholds whereby glucosamine becomes the stimulant in the production of proteoglycans and GAGs. Exogenous glucosamine also stimulates the chondrocytes to produce more collagen and enhance articular cartilage metabolism. Once this cycle is enacted, the metabolic precursors are utilized until the rate-limiting threshold is normalized.

Numerous disclosures suggest the introduction of nutritional supplements as therapy for the treatment of connective tissues. For example, in U.S. Pat. No. 3,682,076 (Rovati et al.) glucosamine sulfates are used to treat arthritic conditions. In U.S. Pat. No. 3,697,652 (Rovati et al.), N-acetyl glucosamine is used to treat degenerative afflictions of the joints. U.S. Pat. Nos. 5,364,845 and 5,587,363 (both to Hederson) show that glucosamine, chondroitin and manganese are used to protect and repair connective tissue. In U.S. Pat. No. 5,840,715 (Florio), N-acetyl glucosamine sulfate, chondroitin sulfate, gamma linolenic acid ercosapentaenoic acid and docosahexaneoic acid, and manganese aspartate are combined to treat arthritis symptoms. U.S. Pat. No. 5,916,565 (Rose et al) teaches a composition comprised of D-glucosamine hydrochloride, chondroitin sulfate, cayenne, ginger, turmeric, yucca, Devil's Claw, nettle leaf, Black Cohosh, alfalfa, and celery seeds to repair and maintain damaged tissues in joints of vertebrates. In U.S. Pat. No. 5,162,303 (Goodman et al.), ascorbate is used as a collagen modifier and a wound and tissue healer. In U.S. Pat. No. 5,922,692 (Marino), glucosamine sulfate and chondroitin sulfate are added to foodstuffs. Finally, in U.S. Pat. No. 4,973,605 (Hershler), methlysulfonylmethane (MSM) is touted as an anti-inflammatory and pain reliever.

Accordingly it is understood, the previous references have been useful to varying degrees; however, none of these prior investigators disclose a complete composition of metabolic precursors, comprising: glucosamine potassium, methylsulfonylmethane, chondroitin sulfate, glucosamine sulfate, glucosamine hydrochloride, N-Acetyl D-Glucosamine, sodium ascorbate, and manganese proteinate, specifically combined to work synergistically as biocatalyst in the production of articular cartilage. Nor do these prior disclosures teach or suggest the use of glucosamine potassium and/or methlysulfonylmethane to facilitate cellular uptake of these vital precursors.

SUMMARY OF THE INVENTION

The primary object of the present invention is the reparation of articular cartilage through oral introduction of a novel combination of metabolic precursors, wherein such precursors are nutritional supplements that are readily absorbed via ingestion. It is also a primary objective of the invention to offer a method by which these nutritional supplements may be ingested in order to produce a chondroprotective effect while assisting in the nutrient transfer within the cells of the articular cartilage.

The present invention is directed to a composition and a method to accelerate the process of articular regeneration by:
  A) providing exogenous chondroitin sulfate to stimulate the production of proteoglycans, glycosaminoglycans, and collagen, inhibit degenerative enzymes excreted by the chondrocytes, synovial cells, and aid in nutrient transportation within the synovial fluid;
  B) providing exogenous chondroitin sulfate in concer with N-acetyl D-glucosamine; increasing the production and availability of hyaluronan through the inclusion of its prime substrates galacktosamine (through chondroitin sulfate assimilation) and—Acetyl D-glucosamine;
  C) providing exogenous glucosamine sulfate sodium to stimulate chondrocyte production of proteoglycans and glycosaminoglycans;
  D) providing exogenous glucosamine hydrochloride and N-Acetyl D-Glucosmine to stimulate chondrocyte production of hyaluronic acid;
  E) providing exogenous glucosamine sulfate potassium to facilitate cellular membrane function within the chondrocytes enhancing the availability of the existing glucosamines and stimulating the production of collagen and proteoglycans;
  F) providing exogenous methlyfonylmethane to regulate proper cellular membrane function by normalizing sulfur content within the body and facilitate the production of collagen, reduce pain and provide anti-inflammatory properties;
  G) providing exogenous sodium ascorbate to scavenge free radicals within the joint capsule, modify type II collagen, assist in the healing of related tissues, and facilitate the utilization of manganese in the biosynthetic pathway; and
  H) Provide exogenous manganese proteinate to catalyze the production of proteoglycans and collagen from glucosamine.

DETAILED DESCRIPTION OF THE INVENTION

The present invention discloses a novel composition of nutritional supplements adapted for oral ingestion, comprised of eight specific metabolic precursors to the production of proteoglycans and collagen. The novel composition provided by the invention works synergistically to repair and replenish articular cartilage, resulting in symptomatic relief of joint pain and inflammation caused by articular cartilage degeneration. In particular, the critical inclusion of glucosamine sulfate potassium and/or methylsulfonylmethane provide a unique delivery system for the associated embodiments of this invention. Their ability to regulate cellular membrane function and nutrient transportation within the articular cartilage enhances the effectiveness of the related metabolic precursors, thereby rendering the compositions of the present invention unique.

The present invention provides glucosamine in all four bioavailable forms as a metabolic precursor to the production of proteoglycans, glycosaminoglycans, collagen, and hyaluronic acid. Previously patented compounds we are aware of have included, glucosamine sulfate sodium, glucosamine hydrochloride, and N-Acetyl D-Glucosamine, alone or in various combinations thereof. While these combinations are effective to varying degrees, a sodium imbalance is achieved, inhibiting full cellular volumizing of the available glucosamine.

The compositions provided by the present invention include glucosamine sulfate potassium in order to stabilize the ionic transfer of nutrients within the cells of the articular cartilage. Sodium ions outside the cell wall are dependent upon potassium ions inside the cell for maintaining the essential balance between tissue fluids. This ionic balance across the cell's outer membrane allows the proper movement of nutrients into, and waste product removal out of the cell. Glucosamine sulfate potassium works in concert with glucosamine sulfate sodium activating the mechanism termed "sodium/potassium pump." Within this synergistic relationship, water, nutrients, and waste products transfer back and forth between the nucleoplasm, cytoplasm, and protoplasm of the cells. Without the proper balance of sodium and potassium, cellular function is less than optimal.

Glucosamine sulfate potassium is hypothesized to be a key factor in achieving this balance, and in determining cellular uptake of glucosamine and chondroitin. Glucosamine sulfate potassium normalizes the sodium/potassium ratio thus achieving the proper physiological balance necessary for metabolic precursor utilization resulting in articular cartilage regeneration.

Methylsulfonylmethane (MSM) has unique properties which aid in the bioavailability of the present invention. MSM provides the essential amino acids, methionine and taurine, cysteine and glutathione; necessary for proper cellular function. Methionine and Taurine enhance cell volumizing while regulating glucose metabolism. Cysteine combines with glutamine to produce and maintain glutathione; the most abundant water-soluble antioxidant found inside tissue cells. This naturally occurring free radical fighting substrate protects the cells of the articular cartilage by inhibiting oxidation of the cartilage matrix. The addition of sodium ascorbate further enhances the positive effects of glutathione by elevating and maintaining intercellular levels of glutathione although the effects are indirect. The inclusion of methylsulfonylmethane in certain embodiments of the present invention provides the necessary elements to protect the protoplasm of the cells and normalize membrane function.

In a presently preferred embodiment the invention provides a unique combination of the metabolic precursors necessary for the production of proteoglycans, glycosaminoglycans, hyaluronic acid, and collagen within the articular cartilage; comprising: chondroitin sulfate, glucosamine sulfate potassium, glucosamine sulfate sodium, glucosamine hydrochloride, and N-Acetyl D-Glucosamine. In another preferred embodiment, the invention provides the unique combination of glucosamine sulfate potassium and methylsulfonylmethane in the compositions of the invention to enhance the effectiveness of the present invention by achieving equilibrium between the cellular fluids, thus increasing the bioavailability of the metabolic precursors therein.

In another embodiment MSM and ascorbate are provided in combination in the compositions of the invention to work synergistically as a chondro-protective antioxidant. Likewise, certain compositions embodied by the invention can further comprise manganese proteinate to serve as a biocatalyst in the conversion of glucosamine to glycosaminoglycans.

Thus, the present invention provides unique combinations of the necessary precursors to articular cartilage regeneration. When taken as directed, and in accordance with the methods set forth herein, the compositions of the present invention aid in the reparation of damaged articular cartilage and stimulates the growth of new articular cartilage; providing symptomatic relief from pain and inflammation associated with articular cartilage degeneration.

In one embodiment the compositions of present invention comprises nutritional supplements useful as biocatalysts which can include, but are not limited to; chondroitin sulfate, glucosamine sulfate potassium, glucosamine sulfate sodium, glucosamine hydrochloride, N-Acetyl D-Glucosamine, methylsulfonylmethane, sodium ascorbate, manganese proteinate, and combinations thereof.

In this embodiment, if the mammal should be an adult equine of about 1100 lbs then the therapeutic amounts of the synergistic nutritional supplements of the composition per unit dosage comprises from between about 300 mg and about 500 mg of methylsulfonylmethane; from between about 2000 mg and about 2800 mg of chondroitin sulfate; from between about 2000 mg and about 2800 mg of glucosamine sulfate potassium; from between about 2000 and about 2800 mg of glucosamine sulfate sodium; from between about 2000 and about 2800 mg glucosamine hydrochloride; from between about 400 and about 800 mg of N-Acetyl D-Glucosamine; from between about 400 mg and about 800 mg of sodium ascorbate; and from between about 100 mg and about 300 mg of chelated manganese proteinate.

In this embodiment, if the mammal should be an adult canine then the therapeutic amounts of the synergistic nutritional supplements of the composition per unit dosage comprises from between about 300 mg and about 500 mg of methylsulfonylmethane; from between about 100 mg and about 400 mg of chondroitin sulfate; from between about 100 mg and about 400 mg of glucosamine potassium; from between about 100 and about 400 mg of glucosamine sulfate; from between about 100 and about 400 mg glucosamine hydrochloride; from between about 30 and about 90 mg of N-Acetyl D-Glucosamine; from between about 30 mg and about 90 mg of sodium absorbate; and from between about 10 mg and about 30 mg of chelated manganese proteinate.

In this embodiment, if the mammal should be an adult feline then the therapeutic amounts of the synergistic nutritional supplements of the composition per unit dosage comprises from between about 50 mg and about 90 mg of methylsulfonylmethane; from between about 20 mg and about 60 mg of chondroitin sulfate; from between about 20 mg and about 60 mg of glucosamine potassium; from between about 20 and about 60 mg of glucosamine sulfate; from between about 20 and about 60 mg glucosamine hydrochloride; from between about 5 and about 15 mg of N-Acetyl D-Glucosamine; from between about 5 mg and about 15 mg of sodium ascorbate; and from between about 0.5 mg and about 5 mg of chelated manganese proteinate.

In this embodiment, if the mammal should be an adult human then the therapeutic amounts of the synergistic nutritional supplements of the composition per unit dosage comprises from between about 1500 mg and about 3000 mg of methylsulfonylmethane; from between about 800 mg and about 1600 mg of chondroitin sulfate; from between about 800 mg and about 1600 mg of glucosamine potassium; from between about 800 and about 1600 mg of glucosamine sulfate; from between about 800 and about 1600 g glucosamine hydrochloride; from between about 100 to about 300 mg of N-Acetyl D-Glucosamine; from between about 100 mg and about 300 mg of sodium ascorbate; and from between about 20 mg and about 60 mg of chelated manganese proteinate.

1) Chondroitin Sulfate is a long hydrophilic chain of repeating sugars. This glycosaminoglycan binds to proteoglycan molecules aiding in water and nutrient transportation within the articular cartilage. Chondroitin in its sulfate form includes galactosamine, a primary substrate of hyaluronan and a disaccharide pathway for proteoglycan synthesis secondary to the hexosamine pathways utilized for glycosaminoglycan production. Chondroitin sulfate chains comprise the space formation of the cartilage matrix and integral parts of the proteoglycan molecule. Chondroitin sulfate stimulates the production of proteoglycans, glycosaminoglycans, and collagen, which are the building blocks of healthy cartilage. Chondroitin sulfate also inhibits the secretion of degenerative enzymes by the chondrocytes within articular cartilage. Chondroitin sulfates are non-toxic and work synergistically with glucosamine to hydrate and repair articular cartilage. Presently preferred compositions and methods of treatment provided by the invention can comprise from about 2 mg to about 6 mg of chondroitin sulfate per pound of body weight depending upon the species being treated and can further be case dependent.

2) Glucosamine is an amino sugar comprised of glucose and an amino acid glutamine. It is an important part of mucopolysaccharides, which provide structure to bone, cartilage, skin, nails, hair, and other body tissues. The presence of glucosamine with the cartilage matrix stimulates the chondrocytes to produce collagen and proteoglycans, the major components of articular cartilage.

A) Glucosamine Sulfate Sodium is an aminosugar bound to a composition of sulfate sodium and is a primary substrate for collagen and proteoglycan production specifically glucosamines sulfate form is a biocatalyst in the conversion of glucosamine to glycoaminoglycans. Presently preferred compositions and methods of treatment provided by the invention can comprise from about 2 mg to about 6 mg of chondroitin sulfate per pound of body weight being species dependent.

B) Glucosamine Sulfate Potassium is an amino sugar composition bound to the mineral potassium. Glucosamine sulfate potassium facilitates cellular membrane function while normalizing the sodium/potassium ratio. In turn glucosamine sulfate potassium aids in the exchange of water, nutrients, and waste products allowing the desired introduction of glucosamine for proteoglycan synthesis. Presently preferred compositions and methods of treatment provided by the invention can comprise from about 2 mg to about 6 mg glucosamine sulfate potassium per pound of body weight being species dependent.

C) Glucosamine hydrochloride is an amino sugar derivative through chemical hydrolysis of hydrochloric acid on disaccharides making it readily bioavailable for the production of hyaluronic acid. In this form glucosamine binds to glucuronic acid directly facilitating and stimulating the chondrocyte production of hyaluronic acid. Presently preferred compositions and methods of treatment provided by the invention can comprise from 2 mg to about 6 mg glucosamine hydrochloride per pound of body weight being species dependent.

D) N-Acetyl D-Glucosamine is a derivative of glucose obtained by chemical hydrolysis of chitin. This polysaccharide is readily soluble in water and extremely bioavailable. N-Acetyl D-glucosamine binds to glucuronic acid as well as galactose making it a precursor to hyaluronic acid, keratin-sulfate and chondroitin sulfate. This unique derivative aids an proteoglycan, collagen and glycosaminoglycan production. N-acetyl D-glucosamine has also been shown to aid in the healing of soft tissue injury. Presently preferred compositions and methods of treatment provided by the invention can comprise from about 0.6 mg to about 1 mg N-Acetyl D-Glucosamine per pound of body weight being species dependent.

3) Methylsulfonylmethane: (MSM) is a naturally occurring bioavailable form of sulfur composed of methionine, cysteine, taurine, and glutathione. MSM's unique amino acid profile assists in the delivery of nutritional components to tissue and is necessary for the synthesis of collagen. Its components regulate glucose uptake while assisting in the formation of disulfide bonds which hold molecular strands of connective tissues together. Glutathione provides antioxidant protection within the cartilage matrix. An essential role of MSM is determining the contour of diverse biomolecules and is essential to the activity of many enzymes that protect and sustain protoplasm. Presently preferred compositions and methods of treatment provided by the invention can comprise from about 4 mg to about 10 mg MSM per pound of body weight being species dependent.

4) Sodium Ascorbate is an electrolyte bound ascorbate providing antioxidant properties. Ascorbate is an essential co-factor as part of an enzyme system. It is responsible for many biochemical functions including 1) Maintenance and repair of all connective tissues especially the collagen component. 2) Biosynthesis of bone, teeth, and cartilage. 3) Enhancing manganese utilization within the body. Presently preferred compositions and methods of treatment provided by the invention can comprise from about 2 mg to about 3 mg sodium ascorbate per pound of body weight being species dependent.

5) Manganese Proteinate: A peptide bound form of the mineral manganese, which plays an important role in the synthesis of glycosaminoglycans, and glucoproteins. Manganese proteinate works synergistically with glucosamine and chondroitin sulfate to produce hyaluronic acid, by-passing the rate limiting steps of proteoglycan and collagen production. Independently it is essential for the maintenance and repair of connective tissue. Presently preferred compositions and methods of treatment provided by the invention can comprise from about 2 mg to about 3 mg manganese proteinate per pound of body weight being species dependent.

The embodiments of the present invention have proven safe and non toxic in the prescribed amounts. Each embodiment provides a specific benefit in relation to the repair and regeneration of articular cartilage. Thus, it can be realized that the compositions of this invention comprised of chondroitin sulfate, glucosamine sulfate sodium, glucosamine hydrochloride, glucosamine sulfate potassium, N-acetyl D-glucosamine, methylsulfonylmethane, sodium ascorbate and manganese proteinate provide a unique combination of ample metabolic precursors which advantageously stimulate the production of glycosaminoglycans including hyaluronic acid, proteoglycans and collagen, thereby assisting the body's natural repair mechanisms and specifically directing the chondrocytes in the production of new articular cartilage. It may also be realized that the presence of glucosamine sulfate potassium and MSM aid in cellular membrane function encouraging nutritional uptake and waste removal within the articular cartilage. It may also be realized that such a composition administered orally or with the aid of a caretaker or veterinarian is digestible and assimilated in mammals. It may also be realized that the composition of this invention is capable of symptomatic relief of pain and inflammation associated with articular cartilage degeneration. For the purpose of intake with the aid of a caretaker or veterinarian, the food source should be selected from oats, hay, corn, sugar and any combination thereof.

EXAMPLES OF THE INVENTION

The following case studies were conducted with mammals. Symptomatic relief in animal behavior and recovery from afflictions demonstrates the efficacy of the composition.

Case Study No. 1: An eleven year old male pure bred German Shepherd weighing 95 pounds presented symptoms of difficulty rising in rear and sinking" of the hind quarters. Further this shepherd became reluctant and soon refused to participate or initiate the game of retrieval with a tennis ball. Physical examination revealed pain when hips were palpated. Preliminary diagnosis was hip dysplaysia. Upon recommendation by veterinarian, a regiment of COSEQUIN (U.S. Pat. No. 5,364,845 to Henderson) was administered for a period of 60 days, improvement in symptoms were insignificant. Difficulty rising and refusal to retrieve were still evident. Cosequin treatments were discontinued and a regiment of the present invention was introduced. Including 600 mg. MSM, 380 mg. chondroitin sulfate, 380 mg. glucosamine sulfate potassium, 380 mg. glucosamine hydrochloride, 380 mg. glucosamine sulfate sodium, 100 mg. N-acetyl D-glucosamine, 100 mg. sodium ascorbate and 30 mg. manganese proteinate divided into two doses administered with the aid of a caretaker or veterinarian with dog food morning and evening. Within 14 days of initial administrations significant improvement in mobility and gait were apparent, interest in retrieval became routine. On day 30 palpation by the veterinarian revealed no pain or discomfort. Relief from symptoms was directly attributed to the introduction of the present invention into the dogs diet.

Case Study No. 2: A ten year old cat weighing ten pounds presented symptoms of a slight limp in hind right leg and refusal to jump onto couch or bed as previously displayed. Veterinarian palpation revealed pain in hind hip and stifle joint. Preliminary diagnosis being degenerative joint disease. A regiment of the present invention was introduced including 70 mg. MSM, 40 mg. chondroitin sulfate, 40 mg. glucosamine sulfate potassium, 40 mg. glucosamine hydrochloride, 40 mg. glucosamine sulfate sodium, 10 mg. N-Acetyl D-Glucosamine, 10 mg. sodium ascorbate, 3 mg. manganese proteinate. Divided into two doses administered paternally with the aid of a caretaker or veterinarian with cat food morning and evening. Within 7 days of initial administration symptoms of a limp had vanished, gait had returned to normal. Within 21 days of initial administration the behavior of jumping on couches and beds had returned. Cat remained on present invention for 60 days when administration was halted. After 120 days of initial administration, no prior symptoms of DJD were detectable. Alleviation of symptoms and longevity of relief attributed to use of present invention.

Case Study No. 3: An 18 year old thoroughbred retired after racing career. Currently a broodmare weighing approximately 1200 lbs. diagnosed by veterinarian with ring bone in hind pastern and degenerative joint disease in knees displayed tactile symptoms of heat and inflammation, while exhibiting difficulty walking and trotting was placed on a regiment of the present invention after aborting pregnancy due to increased load bearing stress. While pregnant, this mare's symptoms worsened in direct relation to the growth of foal. By the 5th month of pregnancy, injections of ADAQUAN (an intravenous GAG) were administered; mild symptomatic relief was evident but short lived. By the $7^{th}$ month she was unable to walk and refused to eat, resulting in stress related abortion of the foal. Subsequently the mare was examined and no uterine abnormalities were detected. The current invention was introduced with the aid of a caretaker or veterinarian including 4 g. MSM, 2.4 g. glucosamine sulfate potassium, 2.4 g. chondroitin sulfate 2.4 g. glucosamine hydrochloride, 2.4 g. glucosamine sulfate sodium, 0.6 g. N-Acetyl D-Glucosamine, 0.6 g. sodium ascorbate, 0.2 g. manganese proteinate. Three months prior to breeding and remained on this regiment through foaling. After twenty days of initial administration outward signs of discomfort walking and trotting had subsided. After forty days of initial administration, tactile symptoms of heat and inflammation in the joint areas had dissipated as well. The mare remained on the present invention through foaling without reoccurrence of symptoms. The mare currently remains on the same regiment. The introduction of the present invention into the diet of this mare was directly responsible for increased mobility, pain management, and joint reparation.

Case Study No. 4: A 5 year old gelding thoroughbred race horse weighing approximately 1000 pounds retired early due to trauma of the knees. Veterinarian diagnosis confirmed DJD due to trauma resulting in loss of articular cartilage. This race horse was placed in the Re-Run thoroughbred relocation program yet was un-adoptable due to its inability to support a rider. Tactile symptoms of heat and inflammation were present, walking and trotting were labored and he refused to run with other horses in field. The present invention was introduced including 4 g. MSM 2.4 g. chondroitin sulfate, 2.4 g. glucosamine sulfate potassium, 2.4 g. glucosamine hydrochloride, 2.4 g. glucosamine sulfate sodium. 6 g N-Acetyl D-Glucosamine, 0.6 g. sodium ascorbate, 0.2 g. manganese proteinate, with the aid of a caretaker or veterinarian as a top dressing on grain or feed. Within 14 days of administration heat and inflammation were absent in palpation, walking and trotting appeared normal and brief sprints with the herd were observed. After 30 days re-examination by the veterinarian revealed no pain during palpation. Symptoms of heat and inflammation had disappeared. Behavior in field was observed as that of normal including integrating and running with the herd. No visual symptoms of lameness were apparent. Re evaluation of his status was made, and the gelding was deemed sound for rider and adoptable. The introduction of the present invention was directly responsible for reparation of the articular cartilage in the knees caused by trauma and reversal of related symptoms.

The foregoing examples and case studies had been presented to demonstrate the efficacy of the composition of the current invention. Alleviation and reversal of symptoms related to the degeneration of articular cartilage in these studies is testimony to the direct effect the present invention has in recovery from preexisting afflictions. The resultant benefits can only be attributed to the current inventions ability to repair and stimulate the regeneration of articular cartilage. In each case the introduction of the present invention was paternal, that is, with the aid of a caretaker or veterinarian, and the animals were unaware that treatment was being administered, thus ruling out the "placebo effect."

In each case, introduction of the present invention was identified as the only management variable in the animal's routine. Similar results have been documented with humans, yet clinical trials are unavailable. It is understood that modifications of the present invention may be made without deviating from the intent of this composition. Accordingly it will be appreciated by those skilled in the art that within the scope of the appended claims, the invention may be utilized in alternative methods and all such changes and modifications are considered to fall within the scope of the invention.

What is claimed is:

1. A composition comprised of synergistic nutritional supplements useful for repair of articular cartilage in a mammal, comprising therapeutic amounts of: methylsulfonylmethane; chondroitin sulfate; glucosamine sulfate potassium; glucosamine sulfate sodium; glucosamine hydrochloride; N-Acetyl D-Glucosamine; sodium ascorbate; and chelated manganese proteinate.

2. The composition of claim 1, wherein the mammal is an adult equine and the therapeutic amounts of the synergistic nutritional supplements of the composition per unit dosage comprises from between about 300 mg and about 500 mg of methylsulfonylmethane; from between about 2000 mg and about 2800 mg of chondroitin sulfate; from between about 2000 mg and about 2800 mg of glucosamine sulfate potassium; from between about 2000 and about 2800 mg of glucosamine sulfate sodium; from between about 2000 and about 2800 mg glucosamine hydrochloride; from between about 400 and about 800 mg of N-Acetyl D-Glucosamine; from between about 400 mg and about 800 mg of sodium ascorbate; and from between about 100 mg and about 300 mg of chelated manganese proteinate.

3. The composition of claim 1, wherein the mammal is an adult equine and the therapeutic amounts of the synergistic nutritional supplements of the composition per unit dosage comprises about 400 mg methylsulfonylmethane; about 2400 mg; chondroitin sulfate; about 2400 mg glucosamine sulfate potassium; about 2400 mg glucosamine sulfate sodium; about 2400 mg glucosamine hydrochloride; about 600 mg. N-Acetyl D-Glucosamine; about 600 mg sodium ascorbate; and about 200 mg chelated manganese proteinate.

4. The composition of claim 2, wherein the unit dose is a about a total daily dose for an 1100 lb adult equine.

5. The composition of claim 2 adapted for oral administration and in combination with an equine food source.

6. The composition of claim 5 in wherein the equine food source is selected from the group consisting of oats, hay, corn, a sugar and combinations thereof.

7. The composition of claim 1, wherein the mammal is an adult canine and the therapeutic amounts of the synergistic nutritional supplements of the composition per unit dosage comprises from between about 300 mg and about 500 mg of methylsulfonylmethane; from between about 100 mg and about 400 mg of chondroitin sulfate; from between about 100 mg and about 400 mg of glucosamine sulfate potassium; from between about 100 and about 400 mg of glucosamine sulfate sodium; from between about 100 and about 400 mg glucosamine hydrochloride; from between about 30 and about 90 mg of N-Acetyl D-Glucosamine; from between about 30 mg and about 90 mg of sodium ascorbate; and from between about 10 mg and about 30 mg of chelated manganese proteinate.

8. The composition of claim 7, wherein the mammal is an adult canine and the therapeutic amounts of the synergistic nutritional supplements of the composition per unit dosage comprises about 400 mg methylsulfonylmethane; about 240 mg; chondroitin sulfate; about 240 mg glucosamine sulfate potassium; about 240 mg glucosamine sulfate sodium; about 240 mg glucosamine hydrochloride; about 60 mg. N-Acetyl D-Glucosamine; about 60 mg sodium ascorbate; and about 20 mg chelated manganese proteinate.

9. The composition of claim 7, wherein the unit dose is a about a total daily dose for a 60 lb adult canine.

10. The composition of claim 7 adapted for oral administration and in combination with a canine food source.

11. The composition of claim 1, wherein the mammal is an adult feline and the therapeutic amounts of the synergistic nutritional supplements of the composition per unit dosage comprises from between about 50 mg and about 90 mg of methylsulfonylmethane; from between about 20 mg and about 60 mg of chondroitin sulfate; from between about 20 mg and about 60 mg of glucosamine sulfate potassium; from between about 20 and about 60 mg of glucosamine sulfate sodium; from between about 20 and about 60 mg glucosamine hydrochloride; from between about 5 and about 15 mg of N-Acetyl D-Glucosamine; from between about 5 mg and about 15 mg of sodium ascorbate; and from between about 0.5 mg and about 5 mg of chelated manganese proteinate.

12. The composition of claim 11, wherein the mammal is an adult feline and the therapeutic amounts of the synergistic nutritional supplements of the composition per unit dosage comprises about 70 mg methylsulfonylmethane; about 40 mg; chondroitin sulfate; about 40 mg glucosamine sulfate potassium; about 40 mg glucosamine sulfate sodium; about 40 mg glucosamine hydrochloride; about 10 mg. N-Acetyl D-Glucosamine; about 10 mg sodium ascorbate; and about 2 mg chelated manganese proteinate.

13. The composition of claim 11, wherein the unit dose is a about a total daily dose for a 10 lb adult feline.

14. The composition of claim 11 adapted for oral administration and in combination with a feline food source.

15. The composition of claim 1, wherein the mammal is an adult human and the therapeutic amounts of the synergistic nutritional supplements of the composition per unit dosage comprises from between about 1500 mg and about 3000 mg of methylsulfonylmethane; from between about 800 mg and about 1600 mg of chondroitin sulfate; from between about 800 mg and about 1600 mg of glucosamine sulfate potassium; from between about 800 and about 1600 mg of glucosamine sulfate sodium; from between about 800 and about 1600 g glucosamine hydrochloride; from between about 100 to about 300 mg of N-Acetyl D-Glucosamine; from between about 100 mg and about 300 mg of sodium ascorbate; and from between about 20 mg and about 60 mg of chelated manganese proteinate.

16. The composition of claim 15, wherein the mammal is an adult human and the therapeutic amounts of the synergistic nutritional supplements of the composition per unit dosage comprises about 2000 mg methylsulfonylmethane; about 1200 mg chondroitin sulfate; from between 800 mg and 1600 mg of glucosamine sulfate potassium; from between 800 and 1600 mg of glucosamine sulfate sodium; 1200 mg glucosamine hydrochloride; about 200 mg. N-Acetyl D-Glucosamine; about 200 mg sodium ascorbate; and about 40 mg chelated manganese proteinate.

17. The composition of claim 15, wherein the unit dose is a about a total daily dose for a 200 lb adult human.

18. The composition of claim 15 adapted for oral administration.

19. The composition of claim 1 wherein the composition stimulates chondrocytes to produce, proteoglycans, glycosaminoglycans, hyaluronan, and collagen which repair and rebuild articular cartilage.

20. The composition of claim 1 wherein the composition inhibits degenerative enzymes within the articular cartilage.

21. The composition of claim 1 wherein the composition aids in nutrient transportation within cells of the articular cartilage matrix.

22. The composition of claim 1 wherein the composition provides and optimal delivery system for the present composition as a biocatalyst, elevating and sustaining blood glucosamine potassium and methylsulfonylmethane levels, thereby increasing their bioavailability.

23. The composition of claim 1 wherein the composition provides the necessary components to stimulate synovial cells synthesis of hyaluronic acid.

* * * * *